United States Patent
Similowski et al.

(10) Patent No.: US 8,733,347 B2
(45) Date of Patent: May 27, 2014

(54) DEVICE FOR DETECTING THE IMPROPER ADJUSTMENT OF A VENTILATORY SUPPORT MACHINE USED ON A MAMMAL

(75) Inventors: Thomas Similowski, Issy les Moulineaux (FR); Mathieu Raux, Clermont-Ferrand (FR); Christian Straus, Guyancourt (FR); Patrick Ray, Chatenay Malabry (FR)

(73) Assignee: Universite Pierre et Marie Curie-Paris VI, Paris (FR)

( * ) Notice: Subject to any disclaimer, the term of this patent is extended or adjusted under 35 U.S.C. 154(b) by 823 days.

(21) Appl. No.: 12/373,111

(22) PCT Filed: Jul. 5, 2007

(86) PCT No.: PCT/FR2007/001148
§ 371 (c)(1),
(2), (4) Date: Jan. 9, 2009

(87) PCT Pub. No.: WO2008/006963
PCT Pub. Date: Jan. 17, 2008

(65) Prior Publication Data
US 2009/0241946 A1    Oct. 1, 2009

(30) Foreign Application Priority Data
Jul. 10, 2006    (FR) ..................... 06 06261

(51) Int. Cl.
*A62B 9/00*    (2006.01)
(52) U.S. Cl.
USPC ............. 128/202.22; 128/204.23; 128/204.21
(58) Field of Classification Search
USPC ............. 128/200.24, 202.22, 203.14, 204.18, 128/204.21, 204.23, 204.26, 205.23; 600/300–301, 529, 544–547
See application file for complete search history.

(56) References Cited

U.S. PATENT DOCUMENTS

| | | | |
|---|---|---|---|
| 5,483,969 A * | 1/1996 | Testerman et al. ............ | 600/529 |
| 5,520,192 A | 5/1996 | Kitney et al. | |
| 5,549,655 A * | 8/1996 | Erickson ........................ | 607/42 |
| 6,015,388 A | 1/2000 | Sackner et al. | |
| 6,317,627 B1 | 11/2001 | Ennen et al. | |

(Continued)

FOREIGN PATENT DOCUMENTS

WO    99/43374    9/1999

OTHER PUBLICATIONS

International Search Report dated Feb. 4, 2008, from corresponding PCT application.

(Continued)

*Primary Examiner* — Jackie T Ho
*Assistant Examiner* — Peter S Vasat
(74) *Attorney, Agent, or Firm* — Young & Thompson

(57) ABSTRACT

A device for detecting the improper adjustment of a ventilatory support machine used on a mammal. The device (12) includes measuring elements (40) for taking a measurement, as a function of time, of a neurophysiological signal involved in the respiratory process of the mammal for at least two successive breathing cycles, each breathing cycle comprising a respiratory initiation time; an input for receiving a respiratory initiation signal ($t_o$) which is different from the neurophysiological signal; elements (42) for processing the neurophysiological signals, which are configured to process the neurophysiological signals for each respiratory initiation time over a period of time starting from the respiratory initiation time; and elements (44) for detecting an improper adjustment of the ventilator using the processed signals.

16 Claims, 5 Drawing Sheets

(56) References Cited

U.S. PATENT DOCUMENTS

| | | | |
|---|---|---|---|
| 6,355,003 B1 | 3/2002 | Aviv et al. | |
| 6,390,091 B1 | 5/2002 | Banner et al. | |
| 6,397,845 B1 | 6/2002 | Burton | |
| 6,411,843 B1 | 6/2002 | Zarychta | |
| 6,588,423 B1 | 7/2003 | Sinderby | |
| 2004/0254493 A1* | 12/2004 | Chervin et al. | 600/544 |
| 2005/0081847 A1* | 4/2005 | Lee et al. | 128/200.24 |
| 2006/0074333 A1* | 4/2006 | Huiku | 600/529 |

OTHER PUBLICATIONS

Raux et al., "Influence de la nature volontaire >>ou <<non-volitionnelle >>de la commande respiratoire sur le recrutement motoneuronal diaphragmatique", 5èmes journés de l'eécole doctorale de physiologie et physiopathologie, 2004, Rev Mal Respir 2003, 20, 99.

Raux et al., "Quantification de l'activitédes muscles inspiratoires du cou en ventilation spontanéavec aide inspiratoire", XXXlllème congrès de la sociétéde réanimation de langue française, Sessions Posters, Reanimation, 2005, vol. 14, pp. S174-S175.

Raux et al., "Optimisation de la détection électromyographique de surface de l'activite inspiratoire du scalene".

Chiti et al., "Apport de l'EMG de surface du scalene dans la detection d'une dysharmonie patient-ventilateur", Sessions posters, Reanimation, 2006, vol. 15, pp. S149-S150.

Japanese Office Action, dated Apr. 25, 2012, from corresponding JP application.

Japanese Office Action, dated Aug. 14, 2012, from corresponding JP application.

\* cited by examiner

DEVICE FOR DETECTING THE IMPROPER ADJUSTMENT OF A VENTILATORY SUPPORT MACHINE USED ON A MAMMAL

BACKGROUND OF THE INVENTION

1. Field of the Invention

The present invention relates to a device for detecting the improper adjustment of a ventilatory support machine used on a mammal.

2. Description of the Related Art

Some people suffer from acute respiratory failure resulting, for example, from pneumonia, pulmonary edema or a secondary infection of chronic respiratory diseases. Mechanical ventilatory support may be required. Ventilatory support machines or ventilators comprise means for detecting the patient's inspiration and means for helping the patient to inspire by increasing the airflow or the pressure of the air inhaled by the patient.

Support thus consists in providing a predetermined volume of gas or pressurizing the airways. In both cases, different settings make it possible to adapt the flow of gas to the needs of the patient. The support machine must therefore be adapted to the respiratory behavior of the patient so as to obtain a "harmonious" relationship therebetween, that is to say that the patient has a satisfactory level of physical comfort and does not encounter any respiratory discomfort when using the support machine. If the settings are inappropriate, for example the airflow is too strong or, conversely, too weak, the patient may be uncomfortable or may even become distressed when breathing.

Various means have been used to detect disharmony of this type between the patient and the machine. In particular, it is known to simply ask the patient. However, this is not possible when the patient is asleep or in a coma.

It is also known to monitor ventilatory activity, in particular the frequency and use of the various respiratory muscle groups.

It is also possible to monitor the coordination between respiratory movements and the response of the ventilator in order to detect any asynchronicity or any ineffective actuation of the ventilator.

Lastly, it is known to measure indirect physiological elements which are used to measure ventilatory activity and, if necessary, to detect any desynchronized behavior of the ventilator. Said indirect physiological elements are, for example, occlusion pressure, morphology of the airway pressure curves and ventilatory work.

In practice, these elements must be used sensitively and all constitute indirect indicators of the sensations which the patient may be experiencing.

BRIEF SUMMARY OF THE INVENTION

The object of the invention is to propose a device which makes it possible to reliably detect an improper adjustment of the ventilation machine.

The invention thus relates to a device for detecting the appropriate adjustment of a respiratory support machine used on a mammal, characterized in that it comprises:
  means for measuring, as a function of time, a neurophysiological signal involved in the respiratory process of the mammal for at least two successive respiratory cycles, each respiratory cycle comprising a respiratory initiation time;
  an input for receiving a respiratory initiation signal which is different from the neurophysiological signal;
  means for processing the neurophysiological signals, which means are configured to process the neurophysiological signals for each respiratory initiation time over a period of time comprising the respiratory initiation time and starting before the respiratory initiation time; and
  means for detecting an improper adjustment of the ventilator by means of said processed signals.

The invention thus makes it possible to detect any improper adjustment by means of abnormal neuromuscular or neurological activity in a patient on mechanical ventilatory support. A process of this type enables reliable detection, that is to say detection obtained almost directly from the sensations of the patient.

In accordance with specific embodiments, the device comprises one or more of the following features:
  the processing means comprise means for back-averaging, point-to-point, the neurophysiological signals measured for all cycles over the same specific period of time;
  the measuring means comprise an electroencephalograph and are used to measure possible premotor potential of the mammal before the respiratory initiation time;
  the processing means are configured for calculating the slope of the electroencephalographic signal immediately before the respiratory initiation time;
  the detection means comprise means for comparing the slope with the reference value;
  the reference value is equal to zero;
  the means for detecting an improper adjustment comprise means for triggering an indicator when the value of the slope is greater than the reference value;
  the indicator is an indicator light;
  more than half of said period of time elapses before the respiratory initiation time;
  the measuring means comprise an electromyograph and are used to calculate the integral of an electromyographic signal over said period of time;
  more than half of the period of time elapses after said respiratory time;
  the detection means comprise means for detecting a change over time in the root mean square of the electromyographic signal over said period of time;
  it comprises a sensor for detecting the patient's aspiration, connected to the input for receiving a respiratory initiation signal $t_o$, said sensor being separate from the means for measuring the neurophysiological signal;
  the sensor is a load sensor;
  the sensor is separate from the measuring means.

The invention also relates to a ventilatory support assembly comprising:
  a ventilatory support machine and
  a device for detecting improper adjustment, as described above.

The invention also relates to a method for detecting the improper adjustment of a ventilatory support machine used on a mammal, characterized in that it comprises the steps of:
  measuring, as a function of time, a neurophysiological signal involved in the respiratory process of the mammal for at least two respiratory cycles; each respiratory cycle comprising a respiratory initiation time;
  receiving a respiratory initiation signal $t_o$ which is different from the neurophysiological signal;
  processing the neurophysiological signals for each respiratory initiation time over a period of time comprising the respiratory initiation time and starting before the respiratory initiation time; and detecting an improper adjustment of the ventilator by means of said processed signals.

The invention also relates to computer software comprising instructions which, when said software is loaded onto a computer connected to the means for measuring a neurophysiological signal, carries out the above method.

BRIEF DESCRIPTION OF THE DRAWINGS

The invention will be better understood upon reading the following description, given purely by way of example and with reference to the drawings, in which.

DETAILED DESCRIPTION OF THE PREFERRED EMBODIMENTS

Figure 1:
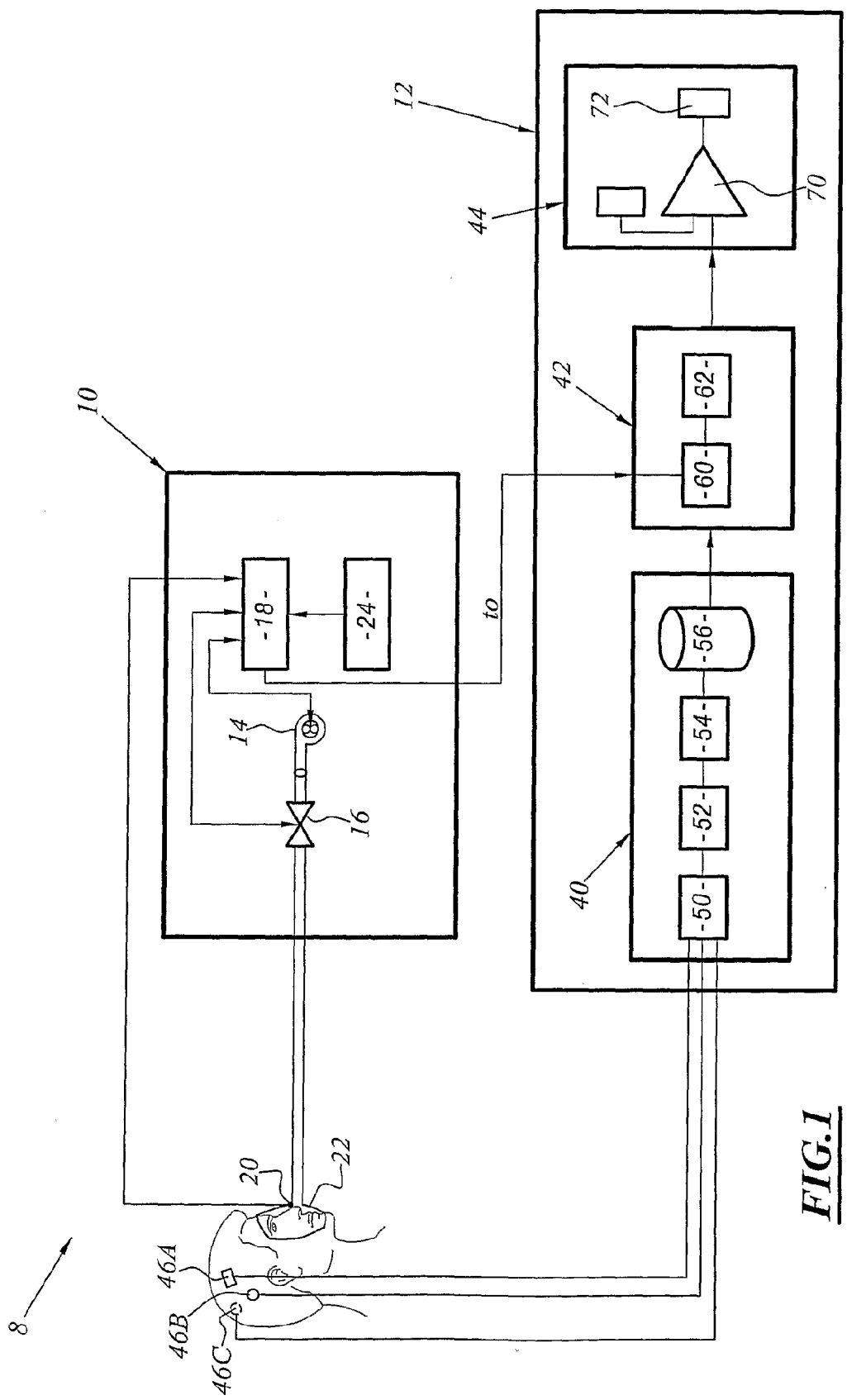
FIG. 1 is a schematic view of a ventilatory support assembly used by a patient.

FIG. 1 shows an example of a ventilatory support assembly 8 which uses a device according to the invention.

Said assembly 8 comprises a mechanical ventilatory support machine 10 and a device 12 for detecting an improper adjustment of the support machine 10.

The machine 10 comprises, as is known per se, a turbine 14 for providing an airflow to a patient at a predetermined airflow rate and at a given pressure. At the output of the turbine 14 a valve 16 is provided for feeding or not feeding the pressurized air produced by the turbine 14 to the patient. The turbine 14 and the valve 16 are connected to a control unit 18 which, in turn, is connected to a load sensor for detecting the patient's aspiration.

The turbine 14 is connected downstream of the valve 16 to a mask 22 which is arranged over the patient's upper airways. The load sensor 20 is arranged, for example, inside the mask 22 of the patient.

In a variation, the mask 22 may be replaced with an endotracheal probe.

The control unit 18 is connected to an adjustment unit 24 for modifying the functioning parameters of the machine 18 and, in particular, the airflow rate produced by the turbine 14, airflow pressure, the switchover times of the valve 16 and any other parameter known from the prior art.

In addition, the control unit 18 comprises an output for providing a respiratory initiation signal $t_o$ which represents the start of the patient's inspiration.

The device 12 for detecting improper adjustment comprises a unit 40 for measuring a neurophysiological signal which represents inspiration and is used to provide a neurophysiological signal as a function of time.

It also comprises a processing unit 42 connected to the measuring unit 40 for receiving the neurophysiological signal. Said processing unit 42 comprises an input for receiving the respiratory initiation signal $t_o$, said input being connected to the corresponding output of the machine 10.

The device 12 further comprises means 44 for providing a doctor with information showing an improper adjustment of the machine 10.

Figure 2:
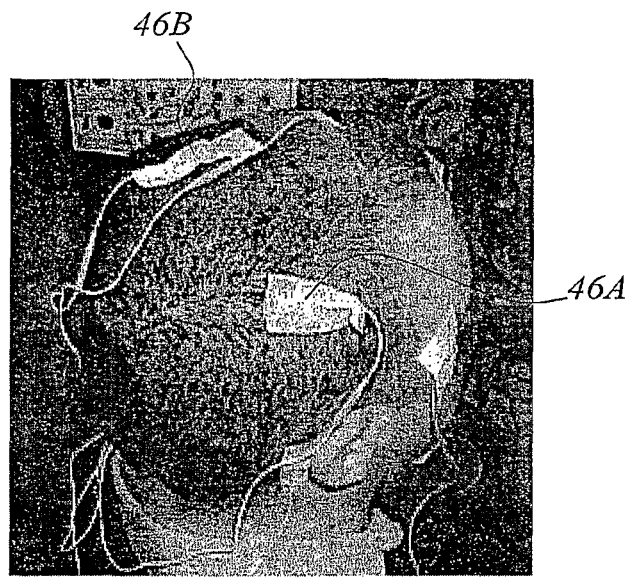
FIG. 2 is a perspective view of the rear three quarters of a human head showing an example arrangement of the electrodes.

According to a first embodiment, the means 40 for measuring a neurophysiological signal are formed by an electroencephalograph. Said electroencephalograph comprises, for example, three electrodes 46A, 46B, 46C arranged on a patient's scalp and, in particular, at the supplementary motor area, that is to say at the premotor cortex. More precisely and preferably, the electrodes 46A, 46B, 46C are arranged at the C3-A+, C4-A+ and Cz-A+ leads of the scalp, as shown in FIG. 2, these positions being defined in the illustration of the international 10-20 system.

As is known per se, the electroencephalograph comprises means 50 for receiving the signal, filtering and amplification means 52 and sampling means 54 for digitalizing the signal, for example with a sampling frequency of 2,000 Hz. It also comprises means 56 for electronically storing the sampled values with their corresponding sampling time.

Figure 3:
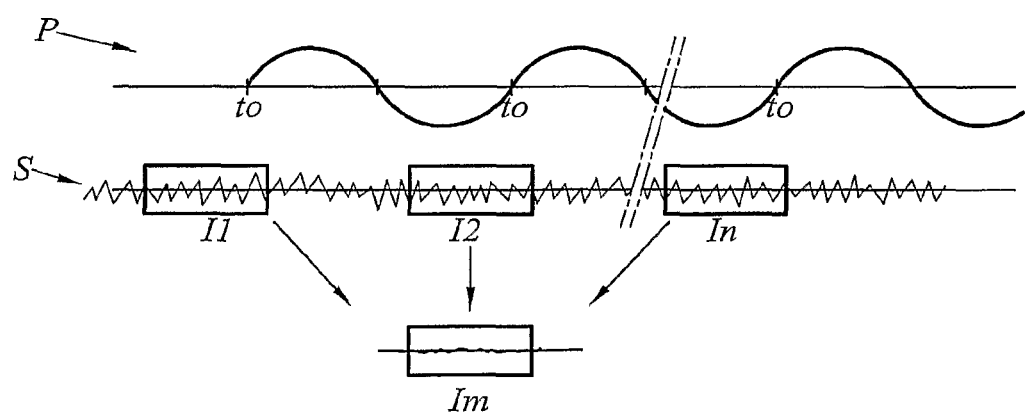
FIG. 3 is a series of curves showing point-to-point averaging over a series of respiratory cycles of the electroencephalographic signal obtained.

The processing means 42 comprise means 60 for back-averaging the sampled values stored over a plurality of respiratory cycles. They are formed, for example, of a microcomputer which uses suitable software. More precisely and as is shown in FIG. 3, the processing means are used to obtain the arithmetic mean, point-to-point, between various successive periods of time $I_1, I_2, I_n$, of the recorded signal, each period of time $I_1, I_2, I_n$ corresponding to a respiratory cycle. Each period of time $I_1, I_2, I_n$ is defined relative to the respiratory initiation time $t_o$ of the corresponding respiratory cycle and comprises said time $t_o$. Respiratory cycle means the period of time constituted by a complete expiration and inspiration.

In FIG. 3, the curve P illustrates the pressure measured by the sensor 20 whilst the curve S illustrates the electroencephalographic signal received at the same times.

The successive periods of time $I_1, I_2, I_n$, from which the signals are averaged, are shown.

They each comprise the respiratory initiation time $t_o$ and have the same duration.

The mean signal labeled $I_m$ is obtained by averaging the signals of the periods $I_1, I_2, I_n$. A mean signal $I_m$ of this type is determined for each of the three electrodes 46A, 46B, 46C. The average is preferably obtained over a number n of successive cycles greater than 10 and, for example, between 50 and 100 and advantageously equal to 80.

The duration of the averaging periods $I_1, I_2, I_n$ is at most equal to the duration of a respiratory cycle. It is preferably between 2 s and 4 s and preferably substantially equal to three seconds.

The averaging period $I_1, I_2, I_n$ includes the respiratory initiation time $t_o$. More than half of this period advantageously elapses before the respiratory initiation time $t_o$. Preferably more than two thirds elapse before the initiation time $t_o$. More precisely, the period starts between 1.5 s and 3.5 s before the respiratory initiation time $t_o$. It preferably starts substantially 2.5 s before.

The period finishes between 0.2 s and 0.7 s and preferably 0.5 s after the respiratory initiation time $t_o$.

The processing means 42 further comprise means for calculating the slope of the averaged electroencephalographic signal observed before the respiratory initiation time $t_o$.

The means 44 for detecting an improper adjustment comprise means 70 for comparing the slope of the average signal $I_m$ with a reference value and means 72 for triggering an indicator, such as an indicator light, when the value of the slope is greater than the reference value.

In practice, said reference value is, for example, equal to zero.

As well as the indicator, the detection means 44 advantageously comprise means for storing and displaying the averaged signals $I_m$ and the values of the slope calculated for each signal $I_m$.

Figure 4:
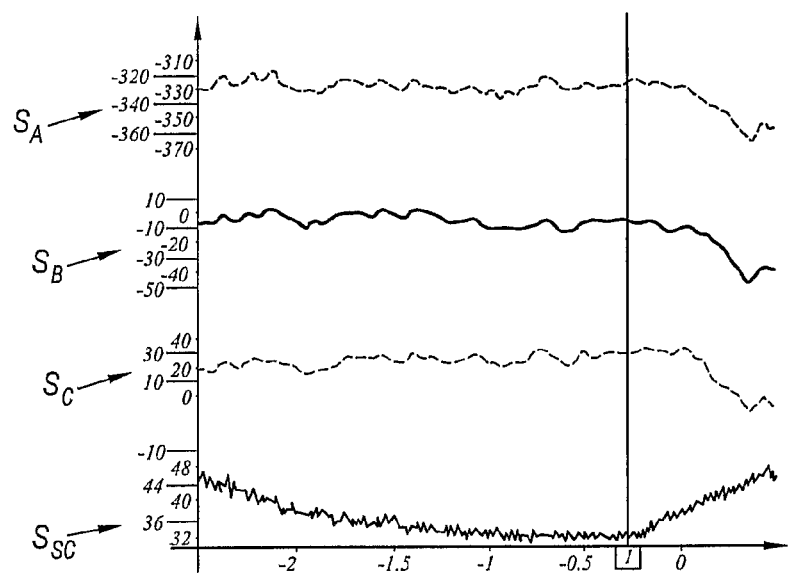
FIG. 4 is an example of a series of curves showing the encephalographic activity detected and the electromyographic activity of the scalene muscle of a human being on ventilatory support.
Figure 5:
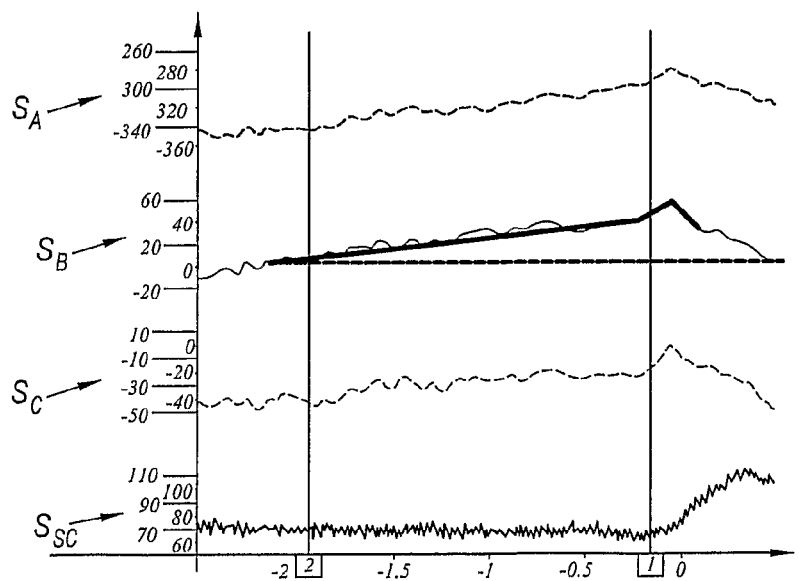
FIG. 5 is an identical view to that of FIG. 4 in the case of disharmony and is an example of a series of curves showing the encephalographic activity detected and the electromyographic activity of the scalene muscle of a human being on ventilatory support.

FIGS. 4 and 5 show an example of the three averaged signal values $S_A$, $S_B$, $S_C$ obtained from the sensors 46A, 46B, 46C on a patient in harmony with the ventilator in FIG. 4 and, in FIG. 5, a patient in disharmony.

It has been found that if the patient and the support machine are in harmony there is no premotor potential before the respiratory initiation time $t_o$, the premotor potential being the electroencephalographic potential measured during the phase immediately before the respiratory initiation time.

In contrast, in the case of disharmony, the premotor potential progressively increases before the respiratory initiation time $t_o$. It is thus assumed that, during disharmony, premotor potential which translates into cortical preparation for movement is established before the initiation time $t_o$.

Since the device is able to detect this premotor potential, it is able to detect disharmony between the respiratory machine and the patient.

From the information provided by the detection means, the doctor is able to modify the settings of the support machine 10 from the adjustment unit 24. In a variation, a control loop is established between the detection means and the support machine 10, the settings being automatically modified as a function of the value of the detected slope of premotor potential.

Figure 6:
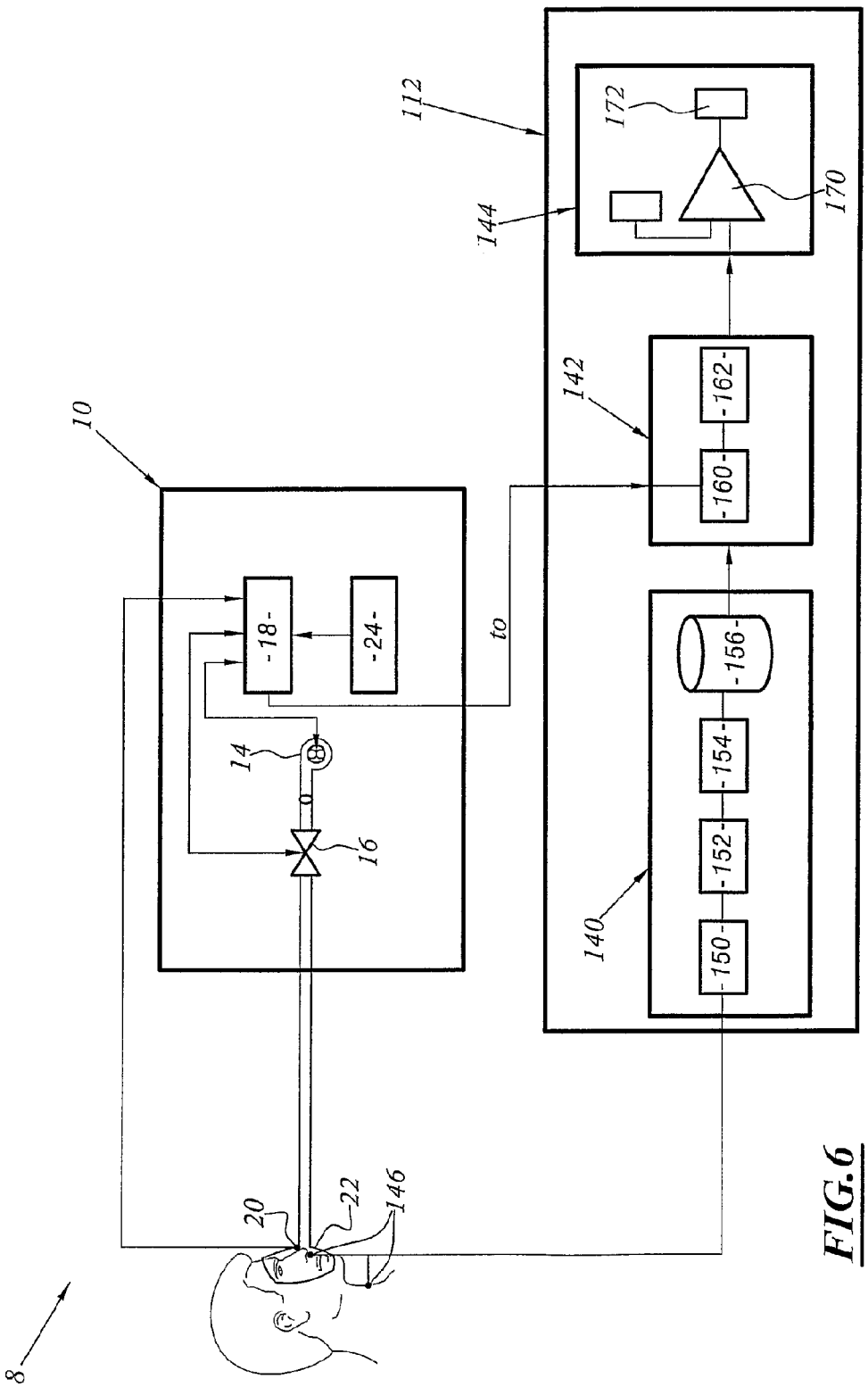
FIG. 6 is an identical view to that of FIG. 1 of a variation of an assembly according to the invention.

According to another embodiment of the device labeled 112 and shown in FIG. 6, the means for measuring a neurophysiological signal are replaced with an electromyograph 140. Said electromyograph comprises one or more electrodes 146 which are placed on the respiratory muscles, that is to say those muscles activated by respiration, for example the muscles of the neck or the face of the patient (in particular the outer walls of the nostrils). These electrodes are able to detect the electrical signals of these muscles. The electrodes are placed, for example, in accordance with a first embodiment on the scalene muscle or, in accordance with a second embodiment, on the alae nasi muscle which controls the opening of the nostrils. In the first case, the electrode 146 is advantageously arranged directly inside the mask 22 ensuring the patient's air supply. The lower signal $S_{SC}$ in FIGS. 4 and 5 shows the recorded electromyographic activity of the scalene muscle.

As before, the device 112 comprises a processing unit 142 connected to the electromyograph 140 and means 144 for revealing information which indicates an improper adjustment.

As is known per se, the electromyograph 140 comprises means 150 for receiving the signal, filtering and amplification means 152 and sampling means 154 having, for example, a frequency of 10,000 Hz, filtering being carried out between 20 Hz and 3 kHz. As before, the electromyograph 140 comprises means 156 for storing sampled values with their corresponding sampling time.

The processing means 142 comprise means 160 for back-averaging the sampled values.

Figure 7:
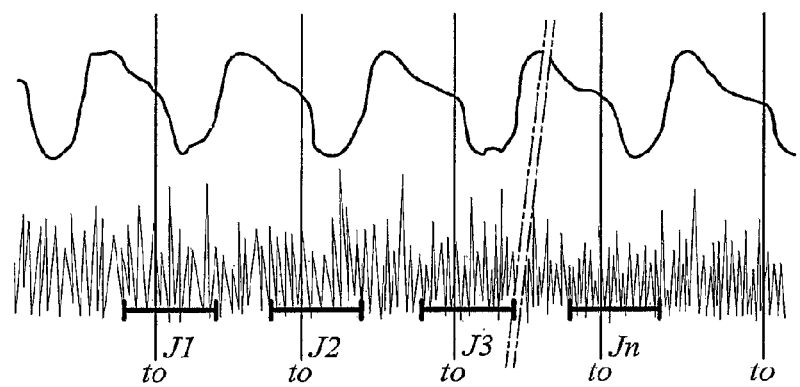
FIG. 7 is an example of a series of curves showing the ventilatory activity (above) and the electromyographic activity (below) for a plurality of respiratory cycles.

With reference to FIG. 7, in this embodiment the processing means 142 are used to calculate the square root of the signal and then the arithmetic mean, point-to-point, of said square root for a number n of pre-determined cycles over periods of time $J_1$, $J_2$, $J_3$, ..., $J_n$ defined relative to the respiratory initiation time $t_o$ of each cycle and comprising said time.

In fact, since in this embodiment the signal is symmetrical relative to the x-axis, it is necessary to make it asymmetrical by squaring it so as to calculate a non zero mean.

The root mean square is advantageously obtained for each period of time $J_1$, $J_2$, $J_3$, ..., $J_n$ over a mobile time window, preferably lasting one millisecond, covering said period so as to obtain an envelope for each period.

The duration of the average period $J_1$, $J_2$, $J_3$, ..., $J_n$ is at most equal to the duration of the respiratory cycle. It is preferably between 2 s and 4 s and preferably substantially equal to 3 s. The period comprises the respiratory initiation time $t_o$. Said period advantageously lasts for more than half and advantageously for more than three quarters after the respiratory initiation time $t_o$. More precisely, the period starts between 0.5 s and 1.5 s before the respiratory initiation time $t_o$. It preferably starts substantially one second before.

The period finishes between 1 and 3 seconds and preferably substantially 2 seconds after the respiratory initiation time $t_o$.

Figure 8:
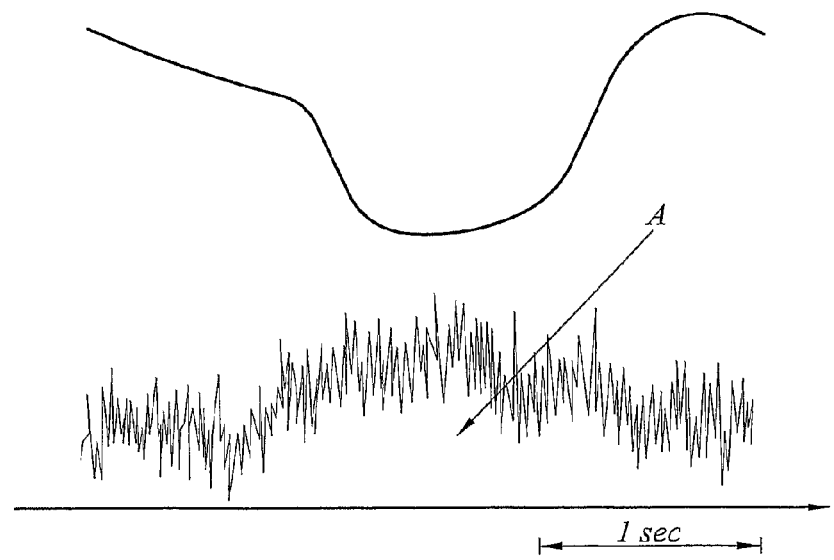
FIG. 8 is a curve showing the ventilatory activity (above) and the mean envelope of electromyographic activity (below).

The processing unit 142 further comprises means 162 for calculating a mean envelope representing the pace of the electromyograms of the preceding n cycles. This mean envelope is shown in FIG. 8 with the scale indicated (1 sec). The envelopes of the various periods $J_1$, $J_2$, $J_3$, ..., $J_n$ are thus averaged in order to obtain the mean envelope. The mean envelope is preferably obtained for a number n of cycles, that is to say periods $J_1$, $J_2$, $J_3$, ..., $J_n$ greater than 10 and between 50 and 100 and advantageously equal to 80.

The means 144 for detecting an improper adjustment comprise means 170 for detecting a change over time in the value of the mean envelope calculated.

The mean envelope is thus stored for various measuring times. Said detection means 170 are used to compare the various values of the mean envelopes stored between periods $J_1$, $J_2$, $J_3$, ..., $J_n$.

A mean envelope is preferably calculated at a frequency of 2 to 15 times per hour and preferably substantially equal to 5 times per hour.

In a variation, the mean envelope is calculated on demand, for example by hospital staff.

If there is no change over time in the value of the envelope, the means 172 do not trigger the indicator for showing an improper adjustment.

In contrast, if there is a change over time in this value and, in particular, an increase in the integral of the mean envelope (denoted as A in FIG. 8), the triggering means are adapted to trigger an indicator.

It has been found that in the case of harmony the value of the integral remains constant. In contrast, in the case of disharmony the integral tends to increase.

Of course the invention is not limited to the embodiment described.

In particular, the way in which the airflow is delivered to the patient is not limited to that which has been described and may be achieved as a volume of administered gas or by pressurizing the airways.

The invention claimed is:

1. A device for detecting an improper adjustment of a ventilatory support machine used on a mammal, the device comprising:
    a measuring device configured to measure, as a function of time, a neurophysiological signal involved in the respiratory process of the mammal for at least two successive respiratory cycles, each respiratory cycle comprising a respiratory initiation time, the measuring device comprising an electroencephalograph;
    an input for receiving a respiratory initiation signal which is different from the neurophysiological signal;
    a processing unit configured to process the neurophysiological signal, the processing unit being configured to select, from the neurophysiological signal, one neurophysiological sub-signal for each respiratory initiation time, each neurophysiological sub-signal being formed by a portion of the neurophysiological signal extending over a period of time comprising the corresponding respiratory initiation time and starting before the corresponding respiratory initiation time, the processing unit being configured to process the neurophysiological sub-signals and to detect an occurrence of a premotor potential before the respiratory initiation time based on the processed neurophysiological sub-signals; and
    a detection unit configured to detect an improper adjustment of the ventilatory support machine based on the processed neurophysiological sub-signals, the improper adjustment being detected when the premotor potential occurring before the respiratory initiation time has been detected by the processing unit.

2. The device according to claim 1, wherein the processing unit is configured to back-average, point-to-point, the neurophysiological signals measured for all cycles over the same specified period of time.

3. The device according to claim 1, wherein the processing unit is configured to calculate the slope of the electroencephalographic signal immediately before the respiratory initiation time.

4. The device according to claim 3, wherein the detection unit is configured to compare the slope with a reference value.

5. The device according to claim 4, wherein the reference value is equal to zero.

6. The device according to claim 4, wherein the detection unit is configured to trigger an indicator when the value of the slope is greater than the reference value.

7. The device according to claim 6, wherein the indicator is an indicator light.

8. The device according to claim 1, wherein more than half of said period of time elapses before the respiratory initiation time.

9. The device according to claim 1, further comprising a sensor for detecting a patient's aspiration, connected to the input for receiving a respiratory initiation signal, said sensor being separate from the measuring device configured to measure the neurophysiological signal.

10. The device according to claim 9, wherein the sensor is a load sensor.

11. The device according to claim 9, wherein the sensor is separate from the measuring device.

12. A ventilatory support assembly comprising:
    a ventilatory support machine; and
    a device for detecting improper adjustment according to claim 1.

13. The ventilatory support assembly according to claim 12, comprising a control loop between the detection unit configured to detect improper adjustment and the ventilatory support machine, the control loop being able to modify settings of the ventilatory support machine.

14. The device according to claim 1, wherein the duration of each neurophysiological sub-signal is at most equal to the duration of a respiratory cycle.

15. A method of detecting an improper adjustment of a ventilatory support machine used on a mammal, the method comprising:
    receiving a measure, at a measuring device comprising an electroencephalograph, as a function of time, of a neurophysiological signal involved in the respiratory process of the mammal for at least two respiratory cycles, each respiratory cycle comprising a respiratory initiation time;
    receiving a respiratory initiation signal, from which the respiratory initiation time is determined, which is different from the neurophysiological signal;
    processing the neurophysiological signal to select, from the neurophysiological signal, one neurophysiological sub-signal for each respiratory initiation time, each neurophysiological sub-signal being formed by a portion of the neurophysiological signal extending over a period of time comprising the corresponding respiratory initiation time and starting before the corresponding respiratory initiation time, and processing the neurophysiological sub-signals and detecting an occurrence of a premotor potential before the respiratory initiation time based on the processed neurophysiological sub-signals; and
    detecting an improper adjustment of the ventilatory support machine based on the processed neurophysiological sub-signals, the improper adjustment being detected when the premotor potential occurring before the respiratory initiation time has been detected by the processing unit.

16. A non-transitory computer software package comprising instructions which, when said software package is loaded onto a computer connected to the measuring device configured to measure a neurophysiological signal, carries out the method of claim 15.

* * * * *